United States Patent [19]

Brewer et al.

[11] Patent Number: 4,880,911
[45] Date of Patent: Nov. 14, 1989

[54] FUSED POLYPEPTIDES AND METHODS FOR THEIR DETECTION

[75] Inventors: Stephen J. Brewer, High Wycombe; Helmut M. Sassenfeld, Benson, both of England

[73] Assignee: G. D. Searle & Co., Chicago, Ill.

[21] Appl. No.: 732,106

[22] Filed: May 9, 1985

Related U.S. Application Data

[63] Continuation-in-part of Ser. No. 471,917, Mar. 3, 1983, Pat. No. 4,532,207.

[51] Int. Cl.$^4$ .................. C07K 15/26; C07K 15/00
[52] U.S. Cl. .................... 530/351; 530/350; 530/324; 530/399; 424/85.4
[58] Field of Search ............. 424/85, 85.4; 530/351, 530/350, 324, 399

[56] References Cited

U.S. PATENT DOCUMENTS

| | | | |
|---|---|---|---|
| 4,046,722 | 9/1977 | Rowland | 424/85 |
| 4,182,695 | 1/1980 | Horn et al. | 424/88 |
| 4,350,764 | 9/1982 | Baxter et al. | 435/68 |
| 4,375,514 | 3/1983 | Siewert et al. | 435/172.3 |

FOREIGN PATENT DOCUMENTS

| | | |
|---|---|---|
| 0001930 | 5/1979 | European Pat. Off. |
| 035384 | 9/1981 | European Pat. Off. |
| 046039 | 2/1982 | European Pat. Off. |

OTHER PUBLICATIONS

Gregory, H., et al.; Int. J. Peptide Protein Res., 9, 107–118, (1977).
Tacon, W., Carey, N. and Emtage, S. Molec. Gen. Genet., 177, 427–438, (1980).
Smith, J., et al., Nucleic Acids Res., 10, 4467–4482 (1982).
Hollenberg, M. D. and Gregory H., Mol. Pharmacol., 17, 314–320, (1980).
Handbook on Affinity Chromatography, Pharmacia Fine Chemicals, Box 175, s–751–04, Uppsala, Sweden.
Ornstein, L. and Davis, B. J., Ann. N.Y. Acad. Aci., 121, 321–427, (1964).
Laemmli, U. K., Nature (London), 277, 680 (1970).
Corbon, M. C., Hugli, T. E. and Muller-Eberhard, H. J., Anal. Biochem., 73, 41–51, (1976).
Imai, K., Bohlen, P., Stein, S. and Udenfriend, D., Arch. Bioch. Biophys., 161, 161–163, (1974).
Eisen, H. N., Immunology, Harper and Row, USA, 395–396, (1974).
Davis, A. R., et al., P.N.A.S. USA, 78, No. 9, 5376–5380, (1981).
Goeddel, D. V., et al., P.N.A.S. USA, 76, 106–110 (1979).
Croft, L. R., Handbook of Protein Sequence Analysis (1980), pp. 468–471.

*Primary Examiner*—Blondel Hall
*Attorney, Agent, or Firm*—Mary Jo Kanady; Paul D. Matukaitis

[57] ABSTRACT

Fused-Polypeptides comprising a polypeptide product and a covalently bonded charged amino acid polymer are disclosed. Methods of detecting the presence of the charged amino acid polymer are used to quantitate the presence of the fused-polypeptides either in crude or purified solutions. The charged amino acid polymer is hydrolyzed using an exopeptidase which leaves the polypeptide product. Examples using polyarginine and carboxypeptidase B to produce urogastrone and gamma interferon are included.

3 Claims, 6 Drawing Sheets

FUSED POLYPEPTIDES AND METHODS FOR THEIR DETECTION

This application is a continuation-in-part of Ser. No. 06/471,917, filed March 3, 1983 now Pat. No. 4,532,207.

FIELD OF THE INVENTION

This invention relates to an improved process for the production of polypeptides produced by genetic engineering techniques.

BACKGROUND OF THE INVENTION

Recombinant DNA technology has now introduced the possibility of producing, for example, pharmacologically-active proteins and peptides in microorganisms. Furthermore, it is possible to introduce changes by means of gene cloning such that the resulting polypeptides or proteins have improved or modified biological activity or stability as compared to the native gene product. However, prior to biological testing and clinical use, it is essential that the peptides or proteins should be purified to a very high degree in order to remove contaminating bacterial proteins, nucleic acids and endotoxins which may cause deleterious side effects. Therefore, there is a need for enhanced methods of purifying proteins produced using recombinant DNA techniques.

Currently, there are numerous methods available to purify peptides and proteins, e.g. affinity, ion-exchange, hydrophobic and molecular sieve chromatography, (see, for example, Williams, B. L., and Wilson, K., Principles and Techniques of Practical Biochemistry, (1975), Edward Arnold, London, 28-123). In order to achieve pure product in high yields and at reasonable cost, considerable development of such methods is necessary. Furthermore, at the moment, different methods must be developed and optimised for each new product. Even small changes in amino acid composition may alter the purification properties such that a modified purification procedure will need to be developed.

A further difficulty in the development of new products by recombinant DNA technology is the assay of the product. Many of the proteins and peptides have no enzymatic activity and may only be determined by either the in vitro or in vivo biological activity thereof. Such assays tend to be inaccurate and time consuming, while purification strategies require large numbers of highly accurate assay results. Immuno-assays based on the highly specific recognition of a protein by an antibody may provide such accurate and rapid assays, (see, for example, Eisen, H.N., Immunology, (1974), Harper and Row, U.S.A., 395-396). However, the raising of antisera to a protein is best achieved by inoculating animals with purified antigen and considerable expertise and time needs to be spent on this task. Also, not only would new antisera need to be raised for each new recombinant product, but because of the high specificity of these antibodies, even small modifications in the amino acid sequence may alter the binding of the product to the antibody and reduce the accuracy of the results.

One approach has been to fuse cloned peptides with a native bacterial protein, e.g. $\beta$-galactosidase ($\beta$-gal) and $\beta$-lactamase (see, for example, Davis A.R., et al. Proc. Natl. Acad. Sci. U.S.A., (1981), 78, No. 9, 5376-5380; and published European Pat. Application No. 35384). Hybrids may then acquire all of the properties of native protein, e.g. convenient assay, established purifications and, in the latter case, secretion from the host cell. However, in the case of $\beta$-galactosidase, ($\beta$-gal), which is a high molecular weight tetramer, the correct association of the $\beta$-gal hybrid subunits may be altered or prevented by the tertiary structure of the hybrid. Although this does not occur when low molecular weight peptides are fused to $\beta$-gal, there is no reason to assume that larger and structurally more complex hybrid proteins will still allow the correct association of subunits to form a fully active enzyme. Without subunit association, recombinants contained the fused polypeptide would not be identified by the $\beta$-gal assay. In a similar manner, the alteration in secondary or tertiary structure of a $\beta$-lactamase fused protein may prevent secretion thereof.

For clinical use, the cloned peptide or protein must be cleaved from the hybrid. Chemical cleavage at methionine residues has been described, but this is of limited use for most peptides and proteins, (see, for example, Goeddel, D.V. et al. Proc. Natl. Acad. Sci. U.S.A., (1979), 76, No. 1, 106-110). To this end, it has been suggested that, by introducing the correct peptide sequence, an endopeptidase might be used to specifically cleave the $\beta$-gal protein from the desired peptide or protein, (see, for example, published European Pat. Application No. 35384). For this approach to work, not only must this cleavage site be unique in the cloned protein or peptide, but also the folding of the entire fused protein must be such that the cleavage site is available to the endopeptidase. Such fused proteins would also share few similarities with the native endopeptidase substrate and the rate of cleavage may be considerably reduced. Furthermore, such endopeptidases could leave amino acids from the cleavage site on the protein of interest thereby making the protein unsuitable for many purposes.

Published European Pat. Application No. 35384 related to DNA sequences coding for amino acid sequences which contain specific cleavage sites. These DNA sequences could be attached to a cloned DNA coding sequence. According to this reference, particularly the amino terminus of an expressed protein may be provided with a removable terminal sequence having distinctive physical properties which are useful for purification. Here it was important that the junction be provided with a cleavage site for an endopeptidase. In an attempt to approach the desired specificity, this prior art advocated the use of extended recognition sites for unusual enzymes. Of course, this procedure would have to be adapted to each protein and subject to the above limitations.

On the contrary, the present improved approach does not depend in the same, way on the structure of the product. By virtue of the use of an exopeptidase, the problem of simultaneous cleavage of the product is obviated without the need for complicated recognition sites for unusual enzymes. More importantly, unlike an endopeptidase, an exopeptidase will not hydrolyze the polypeptide product internally. The present system enjoys a further advantage in that the possibility of assay of the product is provided, which is not foreshadowed in the prior art. In the present case, attention is particularly directed to the carboxy terminus.

The present invention discloses a surprisingly useful process requiring a charged amino acid polymer and an exopeptidase that selectively removes the polymer and that does not harm the desired polypeptide product.

The present invention includes any terminal amino acid polymer and the present invention also includes the use of any exopeptidase, including both aminopeptidases and carboxypeptidases. The polymer may be at either (or both) the amino or carboxy terminals of the desired polypeptide product. Unlike the prior art the present invention allows via genetic engineering the attachment of an easily isolated polypeptide to a protein of interest followed by the selective removal of the attached polypeptide without harm to the protein of interest. In addition, the attached polypeptide serves as an easily quantitated tag reducing the requirement for expensive and difficult bioassays of the protein or its activity. A structural gene is defined as any gene coding for a polypeptide.

SUMMARY OF THE INVENTION

An object of the present invention is the creation of a fused polypeptide comprising a first polypeptide product covalently bonded to a second polypeptide composed of charged amino acids. The charged amino acid polypeptide may contain 2 to 30 amino acids, preferably 3 to 12 amino acids and most preferably 3 to 5 amino acids. An object of the invention is the production of fused-polypeptides where the polypeptide product is urogastrone, trp-E fused urogastrone, or an interferon. An object of the invention is the quantation of the fused-polypeptide using HPLC to separate the fused-polypeptide from contaminating products.

An object of the present invention is to improve the yield and purity of polypeptide products by the synthesis of peptides containing amino acid polymer ends which can be selectively removed by the action of exopeptidases.

An object of the present invention is to utilize recombinant DNA technology and gene synthesis so as specifically to modify cloned proteins to result in improved purification, stabilization and assay. In general terms, this may be achieved by the introduction of tailored peptides of known sequence at either or both end(s) of the cloned protein.

An object of the present invention is to provide a method of producing a specific polypeptide involving a structural gene contained in a cloning vehicle such as a plasmid expressed in a prokaryotic cell and the isolation of the said structural gene product comprising:

(a) inserting adjacent to the said structural gene at either end a DNA sequence coding for a polymer of charged amino acids;

(b) expressing the said structural gene product and charged amino acid polymer as a fusion product;

(c) separating the said fusion product from contaminents based upon the properties of the said polymer of charged amino acids;

(d) removing the said polymer of charged amino acids using an exopeptidase; and optionally, if further purification is required, (e) isolating the said structural gene product free of the said polymer of charged amino acids.

Yet another object of the invention is a fused polypeptide comprising a first polypeptide covalently bonded to a second charged polypeptide. A preferred object of the invention being a fused polypeptide wherein the second charged polypeptide is bonded to the carboxy-termiuus and comprises (arginine)$_n$ where n is 2 to 30. Still another object of the invention is a fused polypeptide where a first polypeptide, either tryp E-fused or normal urogastrone, is covalently bonded to a second peptide, polyarginine; where the polyarginines is 2 to 30 amino acids, or more preferably 3 to 12 amino acids or most preferred 3 to 5 amino acids. As shown in the examples polyarginine is one charged amino acid polymer or "tag" useful in the present invention.

In addition to the polyarginine "tag" other amino acids may be used as a peptide "tag." Peptide "tags" may be designed to include amino acids which modify, for example, the hydrophobicity, the charge or the chemical properties of the product. This allows the production of a peptide conjugate having unusually high affinity on, respectively, hydrophobic interaction, ion-exchange or covalent chromatography, for example. Furthermore, certain characteristics of the peptide tag may be used for affinity chromatography or gel filtration or , for example, dye ligand or antibody columns, (see, for example, Lowe, C. R., and Dean, P. D. G., Affinity Chromatography, (1974), John Wiley and Sons, New York).

Thus, the addition of the peptide tag allows the prediction of specific purification properties of the fused polypeptide and so the rapid purification of the cloned product may be achieved.

Fused polypeptides containing a charged amino acid tag are easily quantitated, even in crude extracts, by assaying for the presence of the charged amino acid tag. This avoids the often tedious and expensive biological assays needed for the final protein product. Methods for quantitating the amount of fused polypeptide present as an indication of final product include HPLC and antibody binding.

Also, the present invention encompasses the use of further "negative" purification techniques. The specific removal of the peptide tag means that the contaminating products that were co-purified with the desired conjugate using, for example, a chromatography step, will still be made to bind to the same chromatography column, while the cloned peptide or protein will not.

The added peptide sequence may be required to be removed to assist in the purification and to provide material for biological testing and clinical use. This may be achieved by including specific amino acids or amino acid sequences within the tag which are susceptible to the enzymatic cleavage.

In general, enzymatic hydrolysis may be achieved using either an endopeptidase or an exopeptidase or combinations of these enzymes. However, in accordance with the present invention, greater specificity and control of hydrolysis is achieved using an exopeptidase, either an aminopeptidase or a carboxypeptidase. By the use of enzymes with defined specificity it is possible to limit the amount of peptide removed from either the carboxy terminus or the amino terminus until the required protein or peptide is produced, (see, for example, Ambler, R. R., Methods in Enzymology, (1968), Academic Press, New York, 11, 155–166). For example, carboxypeptidase B is specific for the basic amino acids arginine and lysine and will not digest other carboxy-terminal amino acids at a significant rate. In contrast, carboxypeptidase A has a wider substrate specificity but it digests arginine and lysine very poorly. Hence, for example, by the complimentary action of these two readily available and well characterized carboxypeptidases, very careful control over the digestion of a carboxy-terminus can be achieved. In doing this the carobxypeptidases can be used either simultaneously or sequentially to digest the carboxy-terminus. Furthermore, as it is highly unlikely that any contaminating proteins will have the particular sequence in the peptide tag at the amino or carboxy ends, very little alteration in their properties, therefore will occur. Therefore, the negative purification step described above may be used to greater effect.

The efficiency of the exopeptidase may be increased in large scale processes by recycling using enzyme reactor systems. The reaction may be monitored by simple assay techniques, e.g. potentiometrically, (see, for example, Walsh, K. A., and Wilcox, P. E., Methods in Enzymology, (1970), Academic Press, New York 19, 35–38), and the efficiency checked by identification of released amino acids, or peptides using, for example, an amino acid analyzer, (see, for example, Light A., Protein Structure and Function, (1974), Prentice Hall Inc., New Jersey, 107–121).

It is also advantageous that the peptide tag should not prevent a recombinant protein from assuming its native conformation. By fusing the peptide tag at the carboxy-terminus, the polypeptide folding is less influenced by the additional amino acid sequence, (see for example, Wetlaufer, D. B., Advances in Protein Chemistry, (1981), Academic Press, London and New York, 61–92). A carboxy-terminal protein tag also has the advantage that only those proteins or peptides which have the complete peptide sequence will acquire both the predicted purification properties and assay characteristics.

It is preferable that the peptide tag should be readily accessible to a purification matrix in an aqueous environment, that is, on the surface of the protein. Therefore, a hydrophilic structure would be preferred. It is also preferred that the tag should not undergo chemical reactions with other parts of the molecule, e.g. an excess of thiol groups might affect the cross-linking of a protein or cause polymerization of the conjugate. Therefore, it is preferred to alter the charge properties by using, for example glutamic acid or lysine, rather than the hydrophobic (e.g. using leucine) or chemical (e.g. using cysteine) properties of the conjugate.

The majority of proteins from bacteria are acidic or negatively charged as are nucleic acids and pyrogens. It is therefore, preferred for the peptide tag to confer a net positive charge on the conjugate so that these contaminants may be rapidly removed by ion-exchange chromatography. Of the three positively-charged amino acids, histidine, lysine and arginine, the last-mentioned is the most hydrophilic and highly charged, (see, for example, Wolfenden, R., et al., Biochemistry, (1981), 20, 849–855). It is, therefore, particularly advantageous for the peptide tag to be rich in arginine residues.

The composition of the tag may be varied as desired to suit particular requirements. However, as regards purification and ease of removal, it is preferable to have a simple polymeric structure, e.g. arginine-lysine, or more preferably, a homopolymer of arginine alone, e.g. poly-arginine.

The length of the peptide tag should be such that it does not result in an excessive amount of the cultures nutrients and amino acid pools being used for its biosynthesis or in translation problems or in plasmid instability. It must be long enough, however, to confer the desired properties on the protein. In the case of a homopolymer, some restriction on length will be caused by the availability of tRNA for the homopolymer fragment which may adversely affect protein translation. Again, arginine is particularly useful because six possible codons are available. These DNA triplet codons coding for arginine are CGT, CGC, CGA, CGG, AGA and AGG. They can be used to construct a DNA polymer coding for the synthesis of polyarginine. The DNA sequence coding for a polymer of charged amino acids may be 2 to 30 consecutive triplet codons, 3 to 12 consecutive triplet codons or 5 consecutive triplet codons. For arginine polymers this would require 2 to 30, 3 to 12, or 5 consecutive arginine triplet codons. This DNA may contain either mixed triplet codons with the advantage of reduced tRNA limitations or one triplet codon repeated, depending upon the optimum requirements for utilizing the cell's translation system most efficiently. Bearing in mind these constraints, a peptide tag length of from 2 to 30 amino acids, preferably from 3 to 12 amino acids, and most preferably 3 to 5 amino acids, may be used.

Assay of the product may be achieved by specific chemical characteristics of the tag. These include chemical reactivity (e.g. arginine-rich peptides may be assayed using the Sakaguchi reagent (Sakaguchi, S, J. Bio chem 5, 33 1925), or cysteine-rich peptides by sulphhydrol group reactivity), UV adsorption (e.g. in the case of tryptophan) or specific dye adsorption properties (e.g. for poly-arginine, see, for example, Itzhaki, R.F., Anal, Biochem. (1972), 50. 569–574.)

In addition, antibodies, including monoclonal antibodies, may be raised to the peptide tag and used in competitive binding assays. Again, a homopolymer is the simplest antigen. These may be raised by coupling the peptide tag to an antigenic protein. Specific antibodies to the peptide tag may then be selected, (see, for example, Geller, S., et al., Biochemistry, (1980), 19,3614–3623). The fused protein may then be assayed using immuno-assays, e.g. RIA (radio-immuno-assay) or ELISA (enzyme-linked-immunosorbant-assay). This assay would then be suitable for any other products containing the "tag" which would minimize assay development efforts.

By incorporating the correct sequence of amino acids, it is also possible to protect sensitive proteins from degradation. For example, small hydrophobic peptides may be protected from surface adsorption or denaturation by the presence of a protective charged tag. Protease sensitivity caused by specific or nonspecific bacterial proteases may be reduced by the inclusion of an inhibitory sequence of amino acids. For example see FIG. 1 incorporating polyarginine. These protective sequences may be incorporated into the peptide tag or fused to the other end of the cloned protein from that fused to the peptide tag and removed as described above.

*E.coli* from a culture producing polyarginine tailed urogastrone was incubated with extraction buffer for 24 hours at room temperature, centrifuged and the supernatant analysed by HPLC. Peak I contains the bulk of

*E.coli* contaminants and peak II is polyarginine tailed urogastronge.

Figure 6:
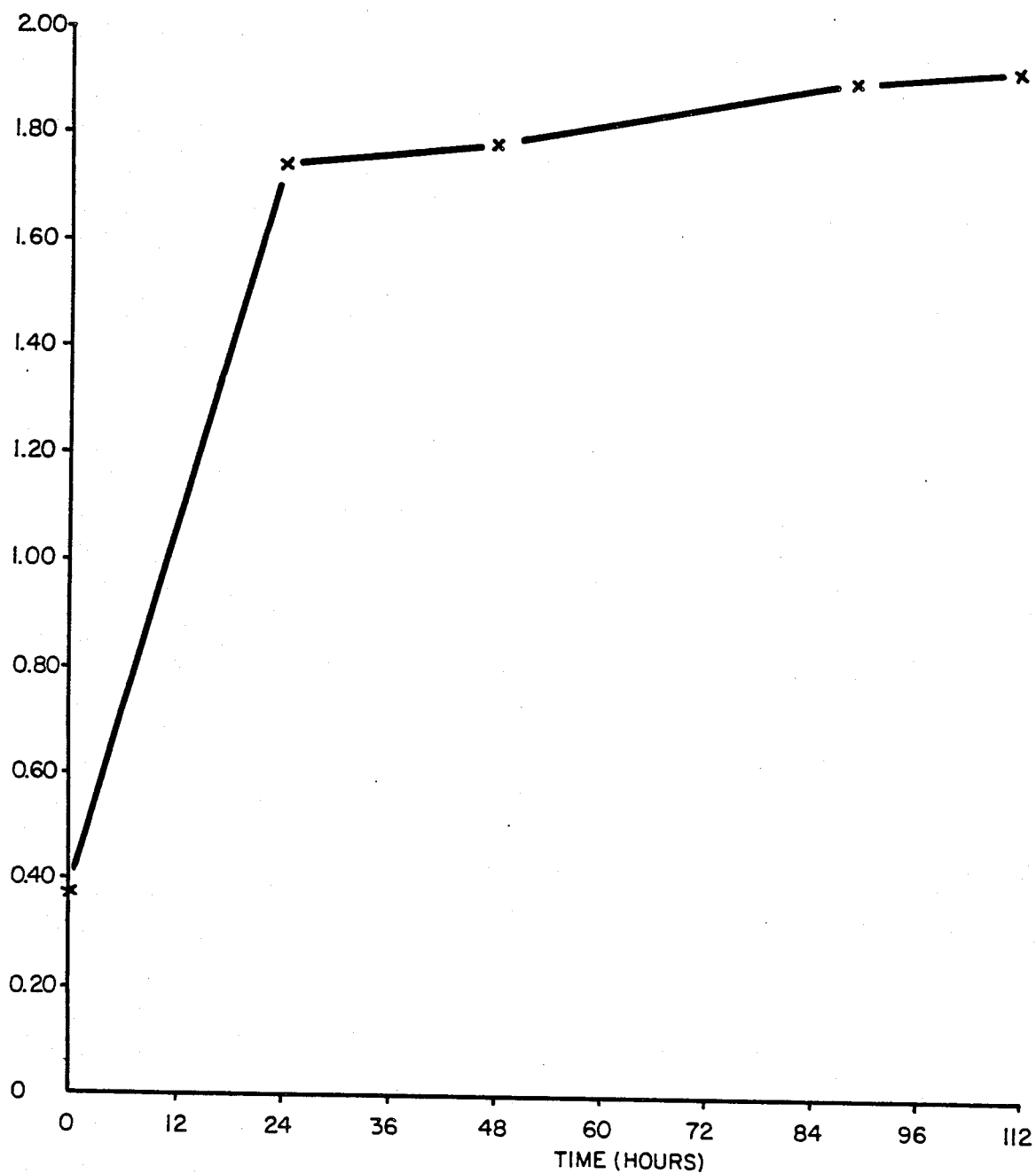

FIG. 6 Time Course of Polyarginine Tailed Urogastrone Extraction from *E.coli*.

*E.coli* from a culture producing polyarginine tailed urogastrone were incubated with urea for different times and samples analysed by HPLC.

Figure 7:
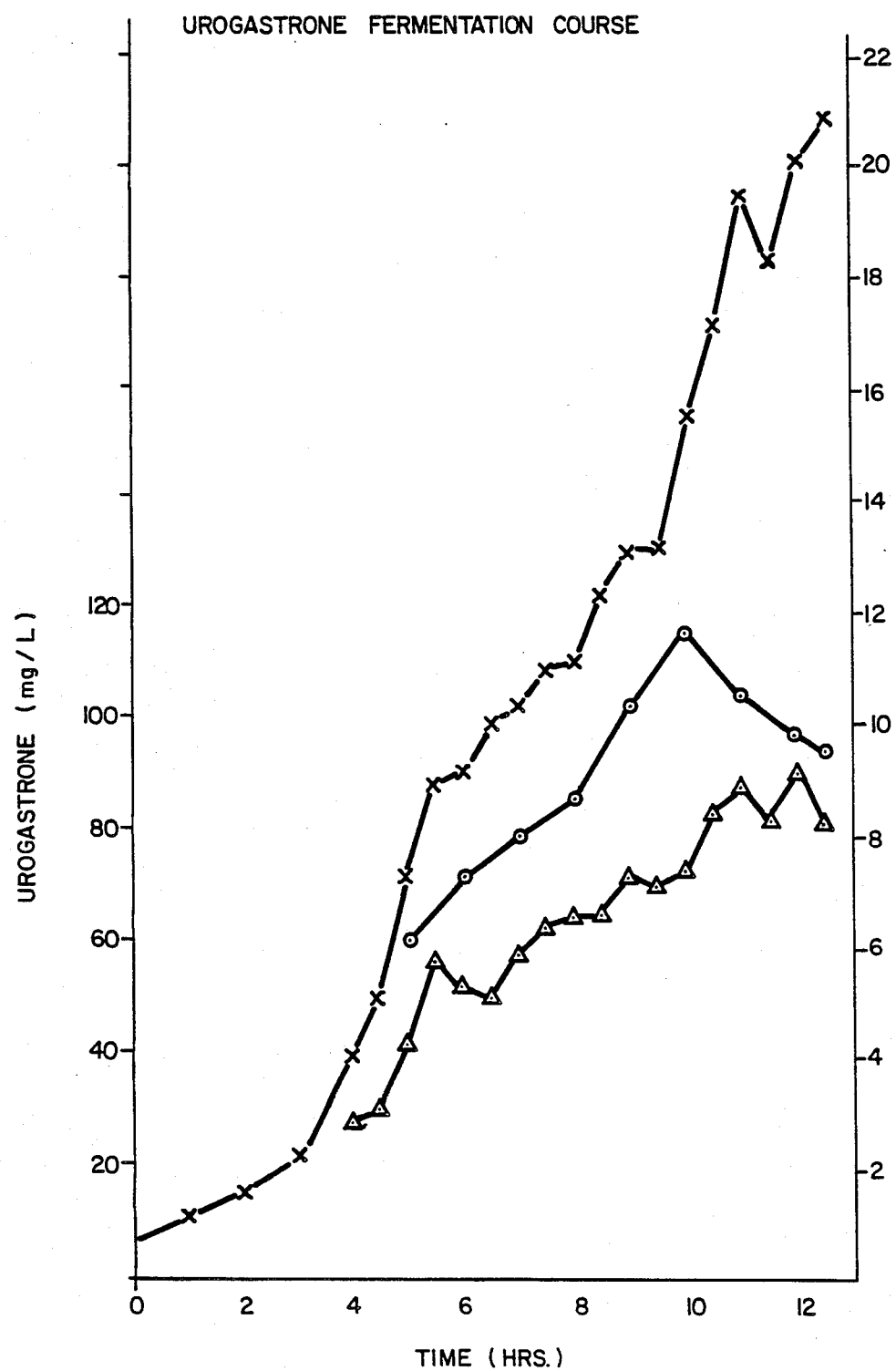

FIG. 7 Time Course of Polyarginine Tailed Urogastrone Production By Cultures of *E.coli*.

*E.coli* samples were taken at different times from a culture producing polyarginine tailed urogastrone and soaked for 24 hours in extraction buffer. The samples were then centrifuged and the supernatant assayed using a RIA (Δ—Δ) and HPLC (O—O) at various times during the fermentation. Growth was followed by measuring the A670 of the culture (X—X).

Figure 8:
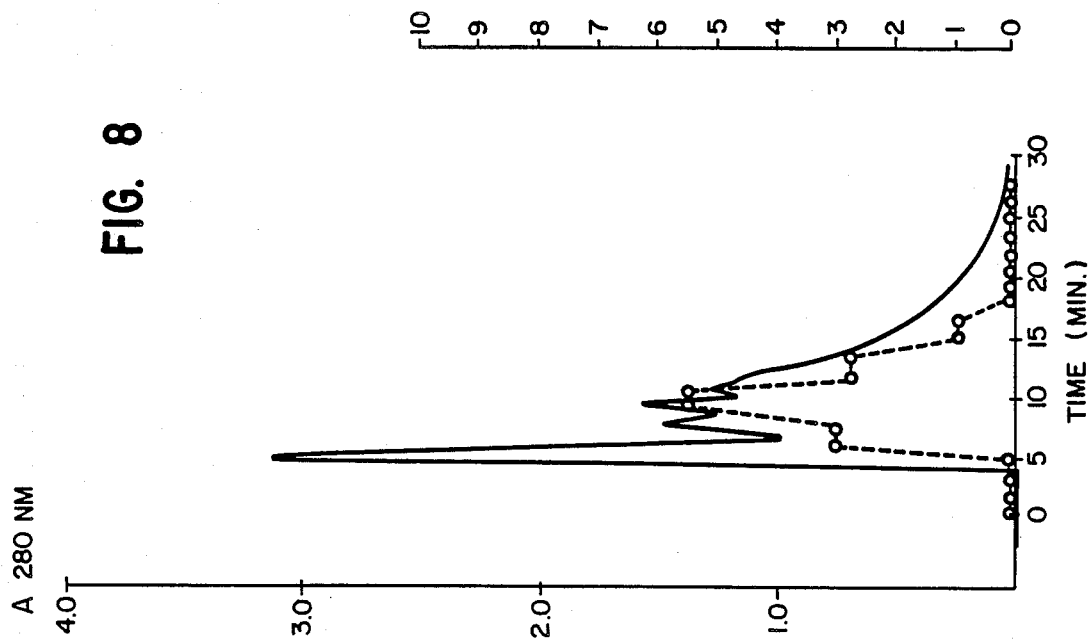

FIG. 8 The elution of polyarg tailed Gamma interferon from Mono S. (O—O) IFN $\times 10^{-6}$ units, —absorbance 280 nm FIG. 9 The elution of Gamma interferon from Mono S. (O—O) IFN $\times 10^{-7}$ units,—absorbance 280 nm.

DETAILED DESCRIPTION OF THE INVENTION

A polymer containing highly charged amino acids, when covalently attached to a polypeptide of interest, serves as a very useful "tag" for the stabilization, isolation and assay of the polypeptide. By attaching a DNA sequence coding for such an amino acid polymer to the gene coding for the polypeptide of real interest, the polypeptide product is synthesized with the amino acid "tag" attached. This "tag" may be either positively or negatively charged at physiological pH. This "tag" may be at either the amino or carboxy terminus of the polypeptide of interest.

The presence of this amino acid "tag" results in stabilization of the polypeptide product, particularly against the action of proteases, but also against other forms of inactivation.

By selecting on the basis of charge, the polypeptide-amino acid tag fusion product can be easily separated from contaminants. Ion exchange chromotography, electrophoresis and isoelectric focusing are among the methods that can be used to isolate the fusion product.

Larger amino acid tags may be needed when larger polypeptide products are to be produced. Similarly, when the polypeptide product has only a slight charge or is neutral a larger charged amino acid polymer may be required.

Removal of the charged amino acid polymer is effected using exopeptidases rather than endopeptidases. Exopeptidases hydrolyze the terminal amino acids of the fusion product sequentially from either the amino or carboxy terminus. Often, the exopeptidases are specific for charged amino acids, resulting in an end to the terminal hydrolysis of the fusion product as soon as the charged amino acid polymer is removed from the fusion product. This results in the release of the polypeptide unharmed and available. One example of such an exopeptidase is carboxypeptidase B which catalyzes the hydrolysis of the basic amino acids lysine and arginine from the carboxyl terminal position in polypeptides.

As an illustration of how such a charged polymer of amino acids is useful in the production of a polypeptide the following experimental system is presented with urogastrone as the polypeptide, polyarginine as the charged amino acid polymer "tag" and carboxypeptidase B as the exopeptidase. Other polypeptides, amino acid tags and exopeptidases can also be used based upon the preceding discussion. They will also function in an analogous manner for polypeptide production.

By conventional nucleotide synthesis techniques, a DNA segment was synthesized which corresponds to the C-terminal portion of urogastrone with additional arginine residues following the native C-terminus, in this case five arginines, which is equivalent to γ-urogastrone (which has similar properties to β-urogastrone except the carboxy terminal arginine is missing) with an additional six arginines. This DNA segment incorporated two restriction sites, one toward the 5' and one at the 3' ends thereof, as well as a stop signal following the fifth arginine. This piece of synthetic DNA was cloned into *E. coli* containing a recombinant urogastrone gene thereby altering the resulting urogastrone C-terminus to contain a polyarginine tag.

The expressed urogastrone protein with its arginine tag was purified and assayed by selectively utilizing the properties of the polyarginine tag.

Purification was effected by means of ion-exchange chromatography on CM-Sepharose CL-6B or SP-Sephadex TM. Following initial purification, virtual homogeneity was achieved by specific removal of the poly-arginine tag and rechromatography on SP-Sephadex. (See Table 1 & 2 and FIG. 3) Efficient removal of the tag was achieved by incubating with immobilized carboxy peptidase B (CPB). (See FIG. 2 and Table 3)

The specificity of the CPB reaction was utilized to assay the expressed protein by determination of arginine released upon hydrolysis with CPB.

The addition of a five amino acid polyarginine tail at the carboxy terminus of β-urogastrone resulted in more than a 3-fold increase in detectable urogastrone synthesized in *E. coli*. This increase in urogastrone might be due, in part, to a decreased rate of protease activity in the presence of the polyarginine.

This additional synthetic DNA sequence was inserted into the β-urogastrone gene which resulted in an additional five arginines at the carboxy-terminus of urogastrone. This was achieved by inserting at the 28 base pair terminal Bgl II-Bam H1 sequence of the synthetic urogastrone gene, a 43 base pair sequence coding for a new carboxy terminus which resulted in a urogastrone protein with the required polyarginine tail. The DNA nucleotide sequence inserted and its corresponding amino acid sequence and restriction sites are shown below.

|  | asp | leu | lys | trp | trp | glu |
|---|---|---|---|---|---|---|
| 5' | GAT | CTG | AAA | TGG | TGG | GAG |
| (restriction site) 3' | AC | TTT | ACC | ACC | CTC |
|  | leu | arg | arg | arg | arg | arg |
|  | CTC | CGT | CGA | CGC | CGT | CGA |
|  | GAG | GCA | GCT | GCG | GCA | GCT |
|  | arg | stop |  |  |  |  |
|  | CGT | TAA | G 3' |  |  |  |
|  | GCA | ATT | CCT | AG 5' (Restriction site) |

To produce quantities of urogastrone this gene coding for urogastrone has been constructed and cloned into *E. coli* using conventional recombinant DNA techniques. Expression of the urogastrone gene was achieved using an expression plasmid utilizing the *E. coli* tryptophan promoter producing a hybrid polypeptide with an additional 14 amino acids at the amino-terminus. The methods used for the expression plasmid were described by Tacon et al. (1980) Molec. Gen. Genet. 177, 427–438 and the methods for the hybrid polypeptide were described by Smith et al. (1982) Nucleic Acids Res. 10, 4467–4482, both articles herein incorporated by reference.

Human gamma Interferon can also be produced utilizing the charged amino acid tag. The fusion-polypeptide was tagged with polyarginine and purification was facilitated as with urogastrone.

The polyarginine tail also changes the migration of the urogastrone-polyarginine hybrid during electrophoresis. This property allows selective purification of the urogastrone analogous to that achieved using ion-exchange chromatography. Similarly, polyarginine specific antibody, either polyclonal or monoclonal, can be used to specifically bind polyarginine-tailed peptides. Through the use of a three step purification process, using either electrophoresis, affinity chromotography or antibody binding as the selective procedure, a pure urogastrone can be achieved. That is, a first step separating polyarginine containing polypeptides of interest followed by a second step where the polyarginine is selectively removed and a third step where the separation process is repeated if necessary. The second separation step removes contaminating molecules that do not have an exopeptidase-sensitive polyarginine region, but which do exhibit polyarginine-like properties during the selective procedure. The result of the three step procedure, separation, exopeptidase and separation, results in essentially pure polypeptide of interest free of the polyarginine tail.

Polypeptide products other than urogastrone and interferon can be prepared using the isolation procedures described. These other polypeptide products include peptide hormones, enzymes, blood clotting factors, antibodies or antibody fragments, peptide cofactors, cytochromes, plasma proteins, structural proteins, peptide antigens, antibiotics and other polypeptides of interest. Among the peptide hormones of interest are the alpha and beta interferons, follicle stimulating hormone (FSH), leukotreins, luteninizing hormone (LH), prolactin, growth hormone, thyroid stimulating hormone, adrenal corticotropin, melanocyte stimulting hormone, parathyroid hormone, calcitonin, corticotropin releasing factor, growth hormone releasing factor, thyrotropin releasing factor, LH releasing factor, prolactin releasing factor, FSH releasing factor, growth hormone release inhibiting factor, endorphins, enkaphalins, vasopressin, oxytocin, proinsulin, insulin, glucagon, relaxin, erythropoietin, secretin, gastrin, progastrin, angiotensin, neurotensin, somatostatin, bombesin, caerulein and other growth effecting peptides. For all hormones both the active form and the prohormone precursor forms are included.

Among the enzymes of interest are the transmethylases, glycosidases, esterases, peptidases, phosphatases, phosphokinases, phosphomutases, sulfatases, sulfotransferases, mutarotases, acyl-coahydratases, fumarases, aspartases, oleate hydratases, isomerases ketothiolases, aldolases and carboxylases.

Of specific interest are the enzymes in the catagories of DNA restriction endonucleases, exonucleases, proteinases, exopeptidases, thrombin and plasmin. For all classes of enzymes both the active form and the zymogen precursor forms are included.

Among the blood clotting factors of interest are
Factor XII (Wageman Factor)
Factor IX (Christmas Factor)
Factor VIII (Antihemophilic Factor)
and Factor X (Steamed Factor).

Among the antibodies and the antibody fragments are the gammaglobulin classes IgG, IgA, IgM, IgE, and the $F_{ab}$ and $F_c$ fragments and the constant regions of both heavy and light immunoglobulin chains.

Among the plasma proteins are included fibrinogen and plasminogen.

Among the structural proteins are included collagen, cell surface peptides and cyto-skeletal peptides.

To produce the polypeptide of interest a synthetic or natural genes, either constructed or isolated from cellular chromosones which code for polypeptides, are modified by the covalent addition of a DNA fragment containing DNA triplet codons directing the synthesis of a polyarginine fragment. This hybrid DNA molecule made according to methods well known in DNA recombinant technology results in the synthesis of a hybrid polypeptide of interest with a polyarginine tail. The methods of this invention are then used as a method of isolating the desired polypeptide. The methods of this invention can be practiced in all cells, both prokaryotic and eukaryotic, including bacteria, yeast, and eukaryotic tissue culture.

EXAMPLE 1

Stabilization of Trp-E Fused Urogastrone by a C-Terminal Polyarginine Fusion The stabilization of urogastrone was demonstrated by the growth of *E. coli* containing the urogastrone-polyarginine gene on plasmids, cell lysis followed by assay for the presence of urogastrone. The following describes the procedures used and the results.

Materials and Methods

Carbenicillin ®, 3β-indoleacrylic acid (IAA), tryptophan and thiamine were from Sigma London Ltd., Poole, Dorset, U.K. Case amino acids were from DIFCO Inc., Detroit, Mich. U.S.A., all other chemicals were analytical grade.

Growth of Cultures: Modified M9 medium (50 ml in 250ml Nunc plastic flasks( containing $Na_2HPO_4.12H_2O$ (15.15 g/L), $KH_2O_4$ (3.00 g/L), $NH_4Cl$ (1.00 g/L), NaCl (0.5 g/L), $Mg_2SO_4.7H_2O$ (0.25 g/L), $CaCl_2.6H_2O$ (2.00 g/L), Case amino acids (5.00 g/L), glucose (5.00 g/L), thiamine HCl (1 mg/L), Carbenicillin Na salt (0.1 g/L) supplemented with Trp (40μg/ml) was inoculated with *E.coli* from a glycerol stock and grown overnight on a New Brunswick Orbital Incubator (18h at 37° C. and 150 rpm) to an $E_{600}$ of 4.3. This culture (5ml) was used to inoculate modified M9 medium (250ml in 800ml plastic flasks) and incubation continued with culture growth monitored by determining the $E_{600}$.

Induction of Urogastrone:- When the $E_{600}$ of the culture reached 0.4, IAA was added (20μg/ml). Samples (2 ml) were withdrawn for lysis and assay of Urogastrone.

Lysis of *E. coli*:- Sucrose buffer (60 μl of 50mM Tris/HCl, pH 7.4; 25% w/v sucrose) was added to culture samples and incubated on ice for 5 min. Additions of lysozyme (20μl of 10 mg/ml in PBS), EDTA (20 μl of 500mM in Tris/HCl, pH 8.0), and Triton X-100 (100 μl of 0.6%) were made with incubation on ice for five minutes between each. Samples were then shaken vigorously at room temperature and stored at −20° C.

Assay of Urogastrone: Lysed samples were thawed, centrifuged (12,000g, 10 min, 4° C.) and the supernatant (0.2 ml) diluted with PBS (1.4 ml). Diluted samples were dialysed (4° C.) against PBS (three changes over 24h) then stored at −20° C. Samples were thawed and assayed using a radio-receptor assay (Hollenberg et al., (1980) Mol. Pharmacology .17, 314–320). Urogastrone receptor activity is expressed as the activity equivalent to a known weight of purified human β-urogastrone standard (uro.equivs.).

Results and Discussion

Figure 1:
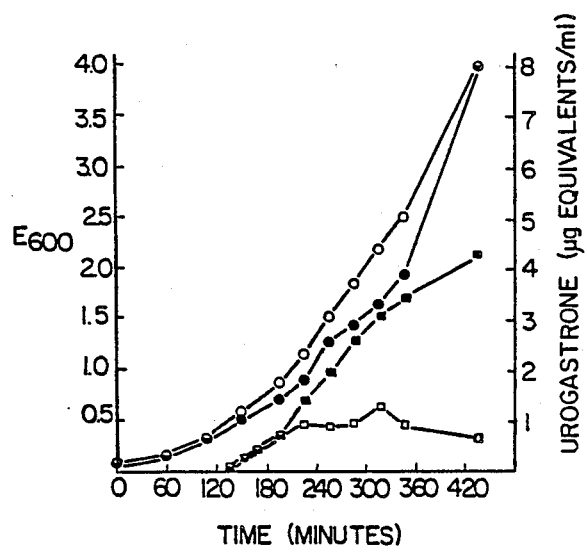
FIG. 1 Expression of the urogastrone gene in *E. coli* with and without a polyarginine tail.

Cultures of E.coli HB101 containing the plasmids PWT221-Uro and the plasmid coding for polyarginine tailed urogastrone, PWT221-Uro-polyarginine, gave similar growth profiles. However, the activity of PWT221-Uro-polyarginine continued to increase throughout the growth cycle whereas PWT221-Uro did not. Furthermore, at the end of the experiment, the activity of PWT221-Uro-polyarginine culture was 3× greater than PWT221-Uro (FIG. 1). The use of modified M9 medium which is low in Trp, and the addition of IAA, the Tryp gene inducer, ensures that the urogastrone gene is being transcribed at its maximum rate. Therefore, if a stable protein is being produced, it should be translated from the mRNA at a constant rate and accumulate throughout the culture's growth. The evidence presented in FIG. 1 indicates that the polyarginine tail is stabilizing the expression and therefore increasing the amount of urogastrone produced by this culture. This may be the result of interactions with anionic polymers associated with the insoluble cell membrane fraction. Such an association may reduce the accessibility of the protein to soluble proteolytic enzymes produced by E.coli.

FIG. 1 illustrates the expression of the urogastrone gene in E. coli with and without a polyarginine tail. E. coli HB101 containing the plasmids PWT221-Uro and PWT221-Uro-polyarginine were cultured and induced with IAA. Growth and urogastrone activity were measured in lysates as described in Methods. Growth (O) and urogastrone activity (□) of PWT221-Uro; growth (●) and urogastrone activity (■) of PWT221-Uro-polyarginine.

EXAMPLE 2

Purification of Trp-e Fused Urogastrone Using the Properties of a Polyarginine Tail The purification of urogastrone utilizing the polyarginine tail was performed on both a small scale (800ml E. coli culture) and a larger scale (32L E. coli culture). The results are shown in Tables 1 and 2. The procedure used was the following.

Materials and Methods

Carboxypeptidase B (CPB) Type 1 DFP (180 units/mg) was obtained from Sigma; SP-Sephadex C-25 ® and CnBr Sepharose were obtained from Pharmacia Fine Chemicals AB, Uppsala 1, Sweden, Spectrapor ® dialysis tubing (cut off 3500) was obtained from Spectrum Medical Industries, Los Angeles, U.S.A. Commassie Blue R250 was from Serva GMBH & Co, Heidelberg 1, W. Germany. Biorad ® protein assay reagent was from Bio-Rad Lab., 8000 Munich 66, West Germany. Pyrotell limulus amoebocyte lysate assay for endotoxins was from Associates of Cape Cod Ltd., Mass., U.S.A. All other chemicals were analytical reagent grade. The 7L fermenter was supplied by LH Engineering Ltd, Stoke Poges, U.K., and the 14L fermenter was supplied by Chemapec Ltd, Abingdon, Oxon, U.K. AVP homogeniser was from AVP Co. Ltd., Crawley, Suffex, U.K.). The sonicator was from Ultrasonics Ltd, U.K.

Fermentation: Shake flask cultures, grown on Modified M9 medium as described in Example 1 were used to inoculate (at 4–10% v/v) either 5L of medium in a 7L fermenter, (stirred at 750 rpm) or 8L of medium with additional glucose.(15 g/L) and Case amino acids (15 g/L) in 14L fermenters (stirred at 550 rpm). All fermentations were at 37° C., pH 7.0, with an aeration rate of one v/v per min.

Urogastrone extraction: Cells were harvested from cultures by centrifugation (4,000 g, 20 mins, 20° C.) and disrupted in lysis buffer (5M urea, 40 mM Tris-acetate/-NaOH pH 9.5) either by a sonicator (30 ml aliquots with a 5 mm probe, 50W, on ice for 10 min) or by an AVP homogenizer (8,000 psi, 2 passes) and centrifuged (16,000 g, 30 mins, 20° C.). The supernatant was adjusted to pH 5.5 with 1N HCl and centrifuged (16,000g for 60 mins, 20° C.). This supernatant was loaded onto SP-Sephadex.

SP-Sephadex chromatography: SP-Sephadex C-25 was equilibrated in Tris/urea (5M urea, 40mM Tris-acetate pH 5.5). All chromatography was performed at room temperature. The flow rate for loading, washing and elution was constant at one bed volume/10min.

Preparation of CPB-Sepharose: CPB (20 mgs in 10 mls of 0.1M $NaH_2CO_3$, pH 8.3) was added to 10 mls of CnBr Sepharose as described by Parmacia (Pharmica, in Handbook on Affinity Chromotography, p 14–18, Uppsala, 1, Sweden.) and reacted for 16 hours at 4° C. Essentially all the protein was coupled to the gel with a 50% recovery of CPB activity. CPB-Sepharose was stable at 4° C. for at least 3 months if stored in phosphate buffered saline (PBS) and azide (0.1%).

CPB digestion: The first SP-Sephadex eluate was digested with CPB-Sepharose by gentle end over end rotation. CPB-Sepharose was removed from digested urogastrone by filtration on a sintered glass funnel.

Gel Analysis: Polyacrylamide gels were prepared by the method of Ornstein and Davis, (Ornstein, L. (1964) Ann. N.Y. Acad. Aci. 121,321–349 and Davis, B. J. (1964) Ann. N.Y. Acad. Aci. 121,404–427). SDS-polyacrylamide linear gradient gels were prepared by the method of Laemmli, (Laemmli, U. K. (1970) Nature (London) 277,680). Gels were fixed and stained using Coomassie Blue (2.5 g/L of methanol:acetic acid:water 3:1:6) and destained in this same solvent mix.

Assays: Bio-Rad dye reagent was used for all protein determinations with BSA as standard. Carboxypeptidase B was assayed using the method of Corbin et al. (Corbin, N. C., Hugli, T. E. and Muller-Eberhard, H. J. (1976) Anal. Biochem. 73,41–51.). Endotoxins were assayed using Pyrogel using the suppliers recommendations. Dry weight was determined after freeze drying.

All other methods are as described in Example 1.

Results and Discussion:

Using a two step ion-exchange process (table 1), the urogastrone from an 800 ml culture was purified to a single band on polyacrylamide gel electrophoresis (PAGE). This purification was based on the loss of positive charge caused by removal of the polyarginine tail with CPB-Sepharose. This change in charge was indicated by the reduction in salt required to elute urogastrone from SP-Sephadex after CPB digestion (30 mM as opposed to 120 mM). This small scale process was successfully scaled up 40 fold to yield 64mgs of purified urogastrone with a good yield (table 2). This preparation has been analysed by gel electrophoresis (single band on SDS-PAGE and PAGE), assayed for endotoxins (lng pyrogen/mg protein), and the dry weight determined (1.3 mgs/mg protein).

The Small Scale Purification of Urogastrone was performed as follows with the results shown in Table 1.

The crude load was from an 800 ml E.coli culture grown in a 7L fermenter to an $E_{600}$ of 2.2 and lysed by sonicaton. The SP-Sephadex column (10 mm×20 mm) was washed with 10 mls of Tris/urea and eluted with a linear gradient (0-300 mM NaCl in Tris/urea). Fractions containing peak Urogastrone activity were pooled, adjusted to pH 8.1 with 1M NaOH and digested with 100μL of CPB-Sepharose for 2 hours at 22° C., pH 8.1. The CPB treated urogastrone was dialyzed overnight at 4° C. against 8L of 40 mM Tris/acetate, pH 5.5; then urea was added to 5M and the CPB digested load was pumped onto a SP-Sephadex column (10 mm×10 mm) in Tris/urea. After washing with 5 mls of Tris/urea, the urogastrone was eluted with a linear gradient (0-125 mM NaCl in Tris/urea) and the urogastrone activity pooled.

TABLE 1

| SMALL SCALE PURIFICATION OF UROGASTRONE | | | | | |
|---|---|---|---|---|---|
| Sample Purification | Volume (ml) | Protein (mg) | Urogastrone (mg equivs) | yield | Factor |
| SP-Sephadex Column 1 | | | | | |
| Crude load | 21 | 121 | 4.4 | (100%) | (1) |
| Non-adsorbed and wash | 26 | 83 | 0.3 | 8% | — |
| Elution pool | 6.4 | 3.6 | 2.4 | 55% | 19 |
| SP-Sephadex Column 2 | | | | | |
| CPB digested load | 6.4 | 3.6 | 2.3 | 53% | 19 |
| Non-adsorbed and wash | 12 | 0 | 0 | 0 | — |
| Elution pool | 5.5 | 1.2 | 1.7 | 39% | 51 |

The Large Scale Purification of Urogastrone was performed as follows with the results shown in Table 2.

The crude load was from a pool of four, 8L cultures grown in 14L fermenters to an $E_{600}$ of 3.2. and lysed by AVP homogenization. The SP-Sephadex column (45 mm ×170 mm) was washed with Tris/urea (900 mls), NaCl (70 mM in Tris/urea) and urogastrone eluted stepwise with NaCl (300 mM in Tris/urea). Peak urogastrone activity was pooled, adjusted to pH 8.5 with 1M NaOH and digested with 10 mls CPB Sepharose for 10 minutes at 22° C. The CPB treated urogastrone was then dialyzed against Tris/urea (two changes of 9L.) overnight at 4° C. The CPB digested load was pumped onto a SP-Sephadex column (47 mm× 30 mm) in Tris-/urea. After washing with 150 mls of Tris/urea, urogastrone was eluted with an NaCl gradient (0-200 mM in tris/urea) and peak urogastrone fractions were pooled.

TABLE 2

| LARGE SCALE PURIFICATION OF UROGASTRONE | | | | | |
|---|---|---|---|---|---|
| Sample Purification | Volume (ml) | Protein (mg) | Urogastrone (mg equivs) | yield | Factor |
| SP-Sephadex Column 1 | | | | | |
| Crude load | 1700 | 15470 | 229 | (100%) | (1) |
| Non-adsorbed and wash | 2500 | 14500 | 82 | 36% | — |
| 70 mM NaCl wash | 800 | 80 | 0 | 0 | — |
| 300 mM NaCl elution | 116 | 696 | 151 | 66% | 14 |
| SP-Sephadex Column 2 | | | | | |
| CPB digested Load | 116 | 696 | 151 | 66% | 14 |
| Non-adsorbed and wash | 480 | 9 | 0 | 0 | — |
| Elution pool | 50 | 64 | 100 | 44% | 105 |

After the first purification stage, the urogastrone appeared as the major band on a SDS-PAGE gel. In contrast, the specific activity of this material would suggest that it was only about 25% pure. This discrepancy was probably due to the presence at this stage of a considerable amount of non-protein impurities such as glycopeptide and lipoproteins which do not stain well with Coomassie Blue. These non-protein contaminants were probably removed by the second SP-sephadex column. The ability of this method to remove non-protein contaminants was further emphasized by the enormous reduction in pyrogen levels (greater than 1 mg/ml in crude to 1 ng/ml in purified). Since CPB digestion of both PWT221-Uro and PWT-221-Uro-polyarginine causes no change in receptor activity, the high specific activity urogastrone resulting from this process was probably due to a loss of activity in the urogastrone standard.)

EXAMPLE 3

Assay of C-Terminal Polyarginine Fused Urogastrone.

Figure 2:
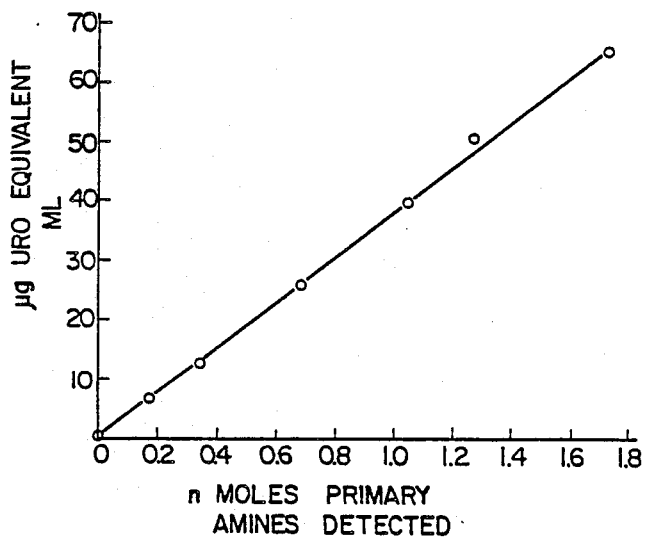
FIG. 2 The assay of polyarginine-tailed urogastrone by the action of carboxypeptidase B releasing primary amines.
Figure 3:
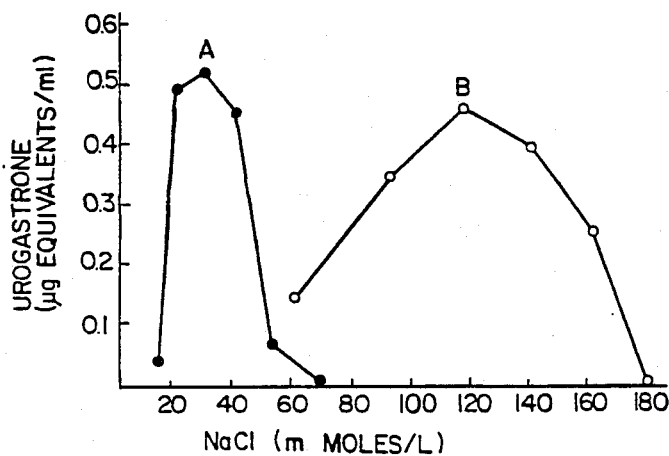
FIG. 3 The elution pattern of urogastrone with and without a polyarginine tail on SP-Sephadex ®.

The polyarginine can be selectively removed from the carboxy-terminus of the urogastrone-polyarginine hybrid by carboxypeptidase B (CPB) without effecting the activity of the urogastrone. The release of primary amines by the CPB is an indication of arginine released. FIG. 2 illustrates the linear relationship between the release of primary amines and urogastrone equivalents present. This indicates that release of primary amines can be used to assay for urogastrone. Release of the arginine by CPB changes the chromatography elution pattern of the urogastrone on SP-Sephadex facilitating purification of urogastrone (FIG. 3, Tables 1 and 2). The procedures used were as follows.

Materials and Methods: Carboxypeptidase B (CPB) Type-1 DFP treated (180 U/mg, 5.6 mg protein/ml), L-arginine, and fluorescamine were supplied by Sigma, U.K. Phosphate buffered saline (PBS) was supplied by Oxoid Limited, Basingstoke, Hants U.K. and made in 1/10 the specified volume of water (10×PBS). The fluorometer was a Gilson Spectra/Glo Filter Fluorometer.

Preparation of urogastrone sample: Polyarginine tailed urogastrone (5 ml) purified on SP-Sephadex as described in Example 2 (table 1) was dialyzed against 10 mM acetic acid (800 ml, two changes over 24 hours, at 4° C.)

Polyarginine Urogastrone Assay: Urogastrone (in 50 μl of acetic acid) was incubated with CPB (in 12.5 μl PBS) and 10×PBS (25 μl) in eppendorfs for 10 minutes at 22° C., pH7.2. TCA (100% v/v, 12.5 μl) was added, and after standing for 10 minutes, precipitated protein was pelleted by centrifugation (13,000g, 3 minutes). The supernatant (50 μl) was assayed for primary amines with fluorescamine using a fluorometer by the method of Imai et al. (1974, Arch. Bioch. Biophys. 161,161–163.) The amount of arginine released was determined using a standard solution of L-arginine (4–40 μMolar) in PBS.

Results and Discussion

The molecular weight of Trp-E fused β-urogastrone with a five arginine tail is 8470 Daltons. Using 1.66 mg urogastrone equiv./mg protein (average for several experiments) as the specific activity for pure urogastrone (see note, Example 2), the molarity of urogastrone protein and the expected release of arginine by complete digestion of the tail can be calculated. In table 3, 0.29 nmoles of urogastrone were digested with CPB and 1.79 nmoles of arginine should have been released. Hence the observed release of 1.75 to 1.82 nmole of primary amines is consistent with the complete digestion of polyarginine tailed urogastrone over a ten-fold range of CPB (0.13–1.3 units). FIG. 2 demonstrates that the release of primary amines by CPB (0.25 units) can be used to measure polyarginine urogastrone concentrations between 7–70 mg uro equiv./ml.

By using an excess of CPB, variables such as temperature, pH, enzyme concentration, and time are not critical. This assay works well with partially purified material, but a number of problems might occur in the crude extract. A small percentage of the bacterial proteins may have C-terminal arginine or lysine, however, provided expression levels are high (2–20%), such proteins are unlikely to increase the apparent titres by a significant amount. Also, primary amines and urea greatly increase the background fluorescence. This problem might be solved by CPB digestion in urea, and adsorption of arginine to a cation exchanger at alkaline pH. Arginine could then be selectively eluted and measured with fluorescamine, however, the best assay for crude urogastrone would be based on monoclonal antibodies directed against the polyarginine tail. Such an assay would also have an advantage over conventional antibody assays by only detecting fully translated polypeptides.

Table 3 shows the release of arginine from polyarginineurogastrone by CPB digestion. Polyarginine-tailed urogastrone (4.2 mg) was prepared, digested with CBP and assayed for primary amines as discussed in the methods.

TABLE 3

Arginine release from polyarginine-tailed urogastrone by Carboxypeptidase B.

| Carboxypeptidase B (units) | Arginine (nmoles) |
| --- | --- |
| 1.3 | 1.82 |
| 0.13 | 1.75 |
| 0.013 | 0.62 |
| 0.0013 | 0.24 |
| 0.00013 | 0.11 |

FIG. 2 illustrates the linear relationship between urogastrone equivalents and the release of primary amines (arginine) during the assay of polyarginine tailed urogastrone by caroxypeptidase B. These polyarginine-tailed urogastrone samples were prepared, digested with CPB and assayed for primary amine release as described in Methods. FIG. 3 illustrates the elution pattern of Urogastrone with and without a polyarginine tail, at various NaCl concentrations from a SP-Sephadex column. The urogastrone was eluted from SP-Sephadex as described in Table 2. The elution of urogastrone before and after CPB treatment is indicated by profiles B and A respectively. (O—O) urogastrone before CPB treatment; (O—O) urogastrone after CPB treatment. Therefore, the removal of the polyarginine tail resulted in a change in the chromatography elution profile of urogastrone and facilitated purification.

EXAMPLE 4

HPLC Assays for Polyarginine Tailed Urogastrone.

HPLC has advantages for the assay of organic molecules in complex and impure mixtures and is the method of choice for many analyses. The high reproducibility and resolution of HPLC means that retention times of chromatographic peaks are highly characteristic of the molecule being assayed. Furthermore, with modern electronics, assessment of areas under these peaks provide accurate quantitation of results. In contrast, assays based on a colorimetric reaction, for example, can be misleading due to interference from other components of the mixture.

With proteins, improved HPLC resins have also enabled HPLC analysis to be developed. These methods work well with purified proteins where they can be used as part of their characterization. However, because all proteins have similar physicochemical properties and diffusion rates are limited by high molecular weights, the resolution of a protein from complex mixtures of other similar proteins, can be exceedingly difficult. Other methods of assay such as those based on immunological recognition of the protein can be misled by the presence of degraded protein species. This is because the antibody recognizes only a small portion (domain) of the protein structure. This domain may well be intact even in degraded protein products. In order to assay crude protein extracts, the protein to be analysed will need to show considerable differences from other contaminants. In the case of polyarginine tailed proteins, we have deliberately altered the physicochemical properties of the protein such that its chromatography profile is very different from other protein contaminants. This means that it is possible to use HPLC to analyse these proteins in crude preparations. Polyarginine fusions for the assay of proteins in fermentation broths and for following extractions from E.coli cells are demonstrated below.

Materials and Methods

HPLC Equipment

Analytical TSK-SP-5PW HPLC columns (3 ml) were supplied by Biorad, Richmond, Calif., U.S.A. The Gilson HPLC with dual pumping system (Model 302) fitted with 5 ml heads. Holochrome UV detector, microcomputer controller and Data Master data collection module, were supplied by Anachem Ltd., Luton, Bedfordshire, U.K.

Buffers

All buffers were made from analar grade chemicals. Urea was ultra-pure and supplied by BRL, Cambridge, U.K. Extraction buffer was 5M Urea, 40 mM-Tris/acetate at pH 9.5. HPLC buffer A was 40 mM MES in 5M urea at pH 6.0 and buffer B was 40 mM MES in 5M urea, 0.5M-NaCl at pH 6.0. Both buffers were freshly prepared, degased and filtered before use.

Chromatography

The gradient was run automatically in 20 minute cycles at a flow rate of 1 ml/min. To ensure complete equilibration of the column, samples were injected onto the column after 18 minutes using a 100 uL loop injector. Separation and analysis was then achieved on the next cycle. Column eluates were analysed by absortion at 280 nM. Data collection was for 15 min from the start of the gradient. The following gradient profile was use in each cycle:

| Time (MIN) | % B | Function |
|---|---|---|
| 0 | 20 | gradient start |
| 9 | 50 | gradient end |
| 10 | 20 | equilibration start |
| 20 | 20 | equilibration end |

Radioimmuno assay (RIA)

The assay was as described by Gregory et al. (1977) JC & M, 45 (4) 668–672.

Standardization

Figure 4:
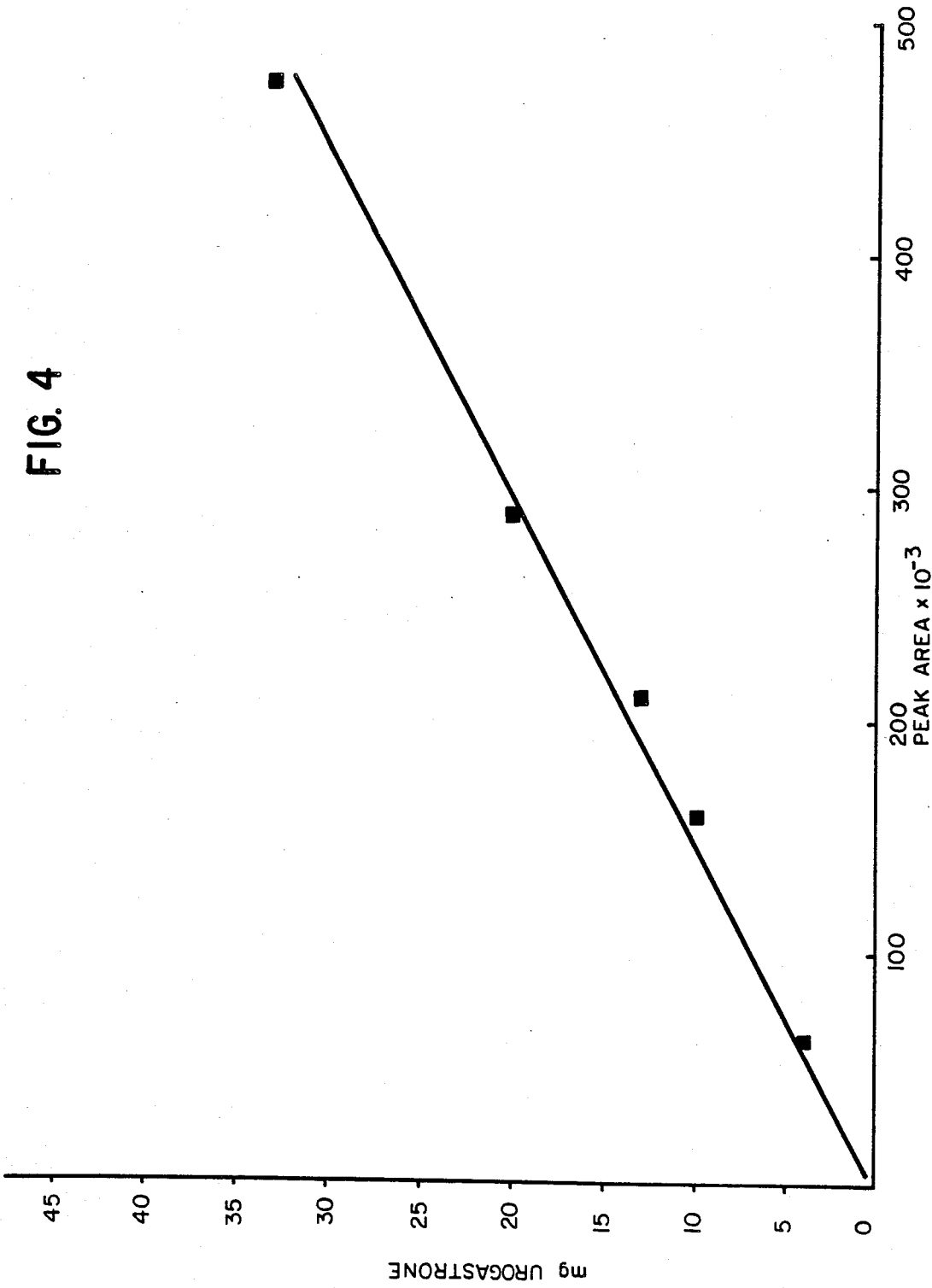
FIG. 4 HPLC Standard Curve for Polyarginine Tailed Urogastrone.

A freeze dried preparation of polyarginine tailed urogastrone purified by preparative HPLC was used as a standard. A weighed sample was dissolved in water to a concentration of 2 mg/ml and diluted into buffer A to provide standards. Areas under the urogastrone peak were integrated. When plotted against the amount of urogastrone in the sample, a straight line was obtained passing through the origin (FIG. 4).

Urea Extraction of Urogastrone from E.coli Cells

Figure 5:
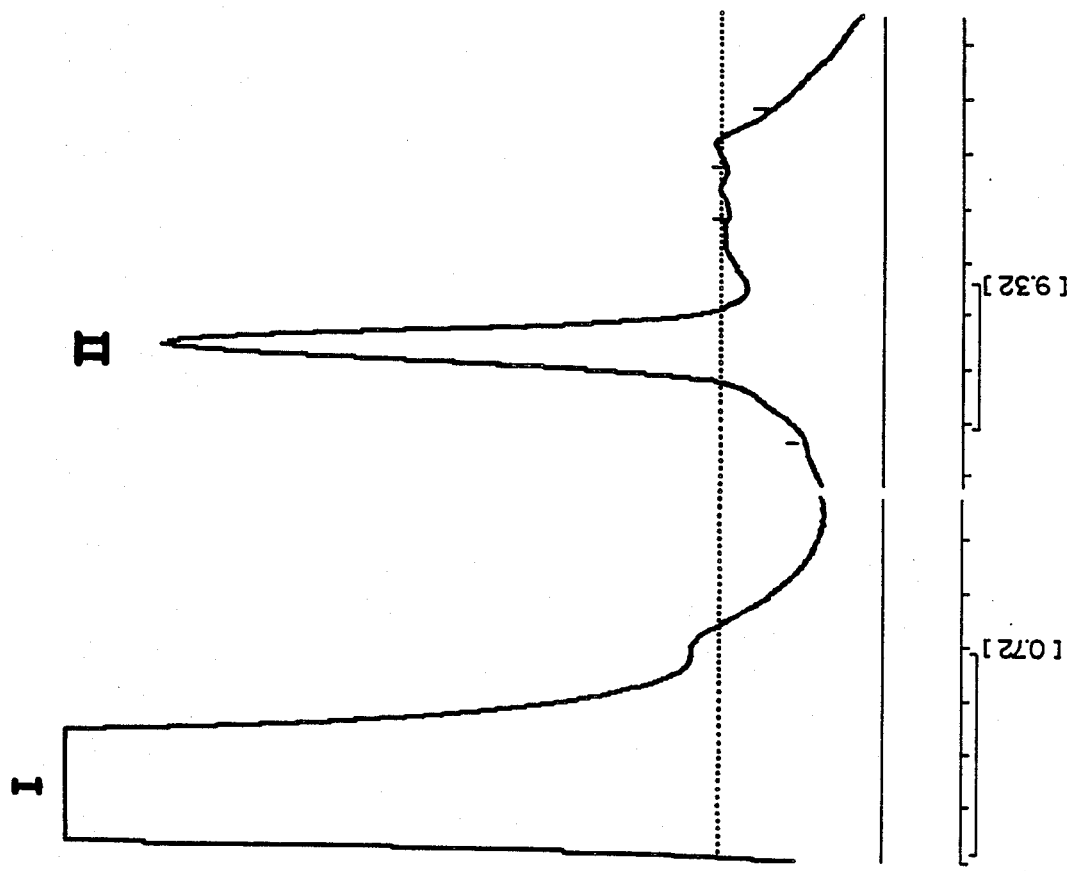
FIG. 5 Analysis of Polyarg-tailed urogastrone in *E. coli* Extracts.

Samples of E.coli from a culture producing polyarginine-tailed urogastrone were extracted by soaking in extraction buffer at room temperature. This permeates the cells and extracts E.coli proteins nucleic acids etc. and also solubilizes urogastrone. Peak I is a large UV absorbing peak caused by the E.coli contaminants (e.g. proteins and nucleic acids). Peak II corresponding to polyarginine tailed urogastrone is clearly separated from the rest of the E.coli contaminants (FIG. 5). This assay enables the time dependent nature of the extraction process to be followed (FIG. 6) and allows optimum conditions to be determined.

HPLC Assay of Urogastrone produced by Cultures of E.coli

Samples were removed from an E.coli fermentation producing polyarginine-tailed urogastrone and analyzed by HPLC and RIA (FIG. 7). It can be seen that whereas the RIA assay shows titres increasing throughout the culture, the HPLC assay shows an optimum before the end of the fermentation. This may be due to the RIA detecting degraded urogastrone produced at this stage of the cultures growth.

EXAMPLE 5

Assay of Polyarginine-Tailed Gamma Interferon Using HPLC.

Materials and Methods

All chemicals used were analytical reagent grade. The sonicator used was an MSE mark II. The HPLC system, including Mono S column, was supplied by Pharmacia Ltd., U.K. The 7L fermenter was supplied by LH Engineering, Stoke Pages, U.K. Nucleases were supplied by Sigma Chemical Co., U.K. HPLC is high pressure liquid chromatography.

Fermentation: Fermentation was essentially as described in patent Example 2 except the temperature was 28° C. and the pH was 6.0.

Gamma Interferon extraction: Cells were harvested by centrifugation (4000 g, 20 mins, 20° C.) and lysed by sonication. To 4.5 gm of a frozen cell pellet was added 50 ml of 0.1M Tris, pH 8 and sonicated on dry ice/ethanol with a 1.5 cm probe for 10 min. at an amplitude setting of 13. The temperature of lysis was 2° C. Cell debri was removed by centrifugation (30,000 g, 35 min, 0° C.). The resulting supernatant was treated with 0.4 mg of a 50–50 w/w mixture of RNase I and DNase I and incubated for 45min at 0° C. before application to a Mono S cation exchange column. (pharmacia)

Mono S chromatography: The 1 ml Mono S column was equilibrated in 0.1 M Tris, pH 8. The flow rate for application, washing and elution was constant at 0.5 ml/min. The prepared lysate (37 ml) was applied; after extensive washing the column was eluted with a linear NaCl gradient (0–2.5M NaCl in 0.1M Tris, pH 8). Column fractions (0.5 ml) were collected and dilutions prepared for CPE antiviral assay (1).

Results and Discussion

Figure 9:
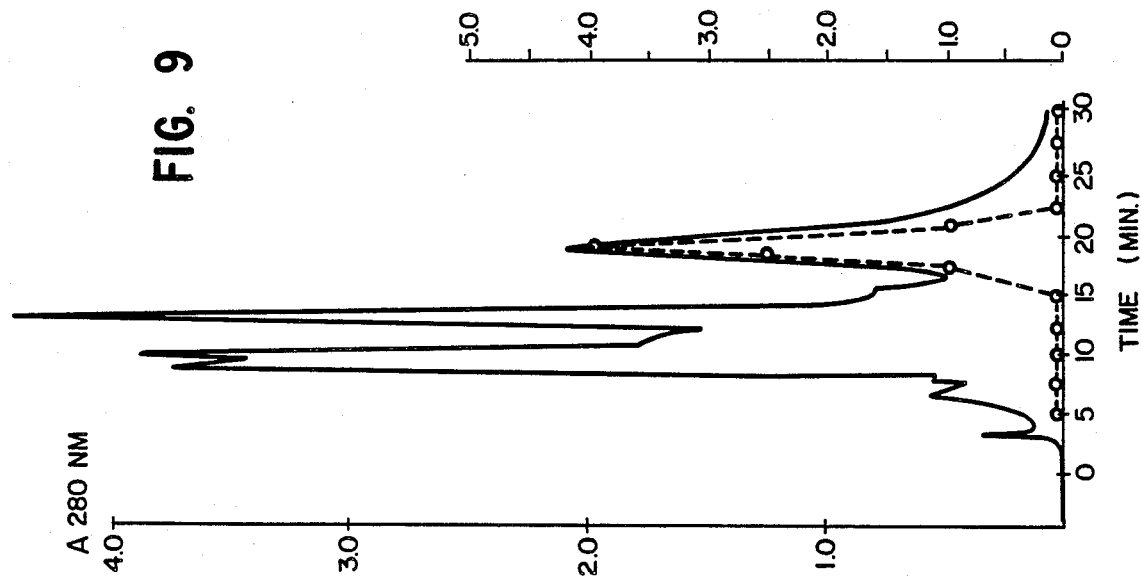

FIG. 8 illustrates the unique retention time of polyarginine-tailed Gamma interferon under the chromotography conditions described above. In marked contrast, FIG. 9 illustrates the retention time of Gamma interferon without a polyarginine tail. Although Gamma interferon is a very basic protein (pI 9.8), its retention time does not adequately distinguish itself from the basic bacterial proteins unless a polyarginine tail is present. As was observed with urogastrone (example 2), a unique retention time is obtained by producing a polyarginine fusion protein.

We claim:

1. A fused-polypeptide comprising urogastrone covalently bonded at its carboxy-terminus to a second polypeptide comprising (arginine)$_n$ wherein n is 2 to 30.

2. A fused-polypeptide comprising trpE-fused urogastrone covalently bonded at its carboxy-terminus to a second polypeptide comprising (arginine)$_n$ wherein n is 2 to 30.

3. A fused-polypeptide comprising human gamma interferon covalently bonded at its carboxy terminus to a second polypeptide comprising

* * * * *

UNITED STATES PATENT AND TRADEMARK OFFICE
CERTIFICATE OF CORRECTION

PATENT NO. : 4,880,911
DATED : Nov. 14, 1989
INVENTOR(S) : Brewer et al.

It is certified that error appears in the above-identified patent and that said Letters Patent is hereby corrected as shown below:

In the Drawings:
Figure #4, Y Axis label reading "mg Urgastrone" should read -- ug Urgastrone --.

Column 2, line 54, reading "in the same, way on" should read -- in the same way on --.

Column 3, line 65, reading "the carboxy-termiuus and" should read -- the carboxy-terminus and --.

Column 6, line 24, reading "(1972), 50. 569-574)" should read -- (1972), 50, 569-574) --.

Column 7, line 2, reading "urogastronge." should read -- urgastrone. --.

Column 10, line 13, reading "lar chromosones which" should read -- lar chromosomes which --.

Column 15, lines 50-51, reading "from polyarginineurogastrone" should read -- from polyarginine-urgastrone --.

UNITED STATES PATENT AND TRADEMARK OFFICE
CERTIFICATE OF CORRECTION

PATENT NO. : 4,880,911

DATED : Nov. 14, 1989

INVENTOR(S) : Brewer et al.

It is certified that error appears in the above-identified patent and that said Letters Patent is hereby corrected as shown below:

Column 18, line 61, reading "comprising" should read -- comprising human gamma interferon covalently bonded at its carboxy-terminus to a second polypeptide comprising (arginine)$_n$ wherein n is 2 to 30. --.

Signed and Sealed this

Twelfth Day of October, 1993

Attest:

BRUCE LEHMAN

*Attesting Officer*  *Commissioner of Patents and Trademarks*